US010405981B2

(12) United States Patent
Hjelle et al.

(10) Patent No.: US 10,405,981 B2
(45) Date of Patent: *Sep. 10, 2019

(54) CARDIAC TREATMENT SYSTEM

(71) Applicant: Mardil, Inc., Plymouth, MN (US)

(72) Inventors: Aaron J. Hjelle, Andover, MN (US); William E. Cohn, Bellaire, TX (US); Richard F. Schroeder, Fridley, MN (US); James F. Buck, Independence, MN (US); Karl R. Leinsing, Dover, NH (US)

(73) Assignee: Mardil, Inc., Plymouth, MN (US)

( * ) Notice: Subject to any disclaimer, the term of this patent is extended or adjusted under 35 U.S.C. 154(b) by 94 days.

This patent is subject to a terminal disclaimer.

(21) Appl. No.: 15/218,675

(22) Filed: Jul. 25, 2016

(65) Prior Publication Data

US 2016/0331880 A1 Nov. 17, 2016

Related U.S. Application Data

(63) Continuation of application No. 14/053,261, filed on Oct. 14, 2013, now Pat. No. 9,421,101.
(Continued)

(51) Int. Cl.
*A61F 2/24* (2006.01)
*A61M 1/12* (2006.01)
(Continued)

(52) U.S. Cl.
CPC ........... *A61F 2/2481* (2013.01); *A61M 1/106* (2013.01); *A61M 1/107* (2013.01);
(Continued)

(58) Field of Classification Search
CPC ...... A61F 2/0013; A61F 2/0031; A61F 2/004; A61F 2/0063; A61F 2/2478; A61F 2/2481; A61F 5/005; A61F 5/0063; A61M 1/1068
See application file for complete search history.

(56) References Cited

U.S. PATENT DOCUMENTS 1,682,119 A 8/1928 Field
1,965,542 A 11/1933 Colvin, Jr.
(Continued)

FOREIGN PATENT DOCUMENTS

DE 324524 8/1920
DE 29517393 2/1996
(Continued)

OTHER PUBLICATIONS

U.S. Appl. No. 09/635,345, filed Aug. 9, 2000, Chin.
(Continued)

*Primary Examiner* — Carrie R Dorna
(74) *Attorney, Agent, or Firm* — Fish & Richardson P.C.

(57) ABSTRACT

An assembly for providing localized pressure to a region of a patient's heart to improve heart functioning, including: (a) a jacket made of a flexible biocompatible material, the jacket having an open top end that is received around the heart and a bottom portion that is received around the apex of the heart; and (b) at least one inflatable bladder disposed on an interior surface of the jacket, the inflatable bladder having an inelastic outer surface positioned adjacent to the jacket and an elastic inner surface such that inflation of the bladder causes the bladder to deform substantially inwardly to exert localized pressure against a region of the heart.

9 Claims, 3 Drawing Sheets

Related U.S. Application Data (60) Provisional application No. 61/713,351, filed on Oct. 12, 2012.

(51) Int. Cl.
    *A61M 1/10*          (2006.01)
    *D04B 21/12*        (2006.01)
    *A61B 90/00*          (2016.01)
    *A61F 2/95*           (2013.01)

(52) U.S. Cl.
    CPC ........... *A61M 1/1008* (2014.02); *D04B 21/12* (2013.01); *A61B 2090/3966* (2016.02); *A61F 2002/2484* (2013.01); *A61F 2002/9517* (2013.01); *A61F 2250/0003* (2013.01); *A61F 2250/0098* (2013.01); *A61M 1/1068* (2013.01); *A61M 1/12* (2013.01); *A61M 1/122* (2014.02); *A61M 2205/32* (2013.01); *D10B 2509/08* (2013.01)

(56) References Cited

U.S. PATENT DOCUMENTS

| | | |
|---|---|---|
| 1,982,207 A | 11/1934 | Furniss |
| 2,138,603 A | 11/1938 | Johnson |
| 2,278,926 A | 4/1942 | Hartwell |
| 2,376,442 A | 5/1945 | Mehler |
| 2,992,550 A | 7/1961 | Frith |
| 3,384,530 A | 5/1968 | Mercer et al. |
| 3,452,742 A | 7/1969 | Muller |
| 3,551,543 A | 12/1970 | Mercer et al. |
| 3,587,567 A | 6/1971 | Schiff |
| 3,643,301 A | 2/1972 | Weigl |
| 3,732,662 A | 5/1973 | Paxton |
| 3,768,643 A | 10/1973 | Bruno |
| 3,811,411 A | 5/1974 | Moeller |
| 3,983,863 A | 10/1976 | Janke et al. |
| 4,035,849 A | 7/1977 | Angell |
| 4,048,990 A | 9/1977 | Goetz |
| 4,196,534 A | 4/1980 | Shibamoto |
| 4,403,604 A | 9/1983 | Wilkinson et al. |
| 4,428,375 A | 1/1984 | Ellman |
| D273,514 S | 4/1984 | Heilman et al. |
| 4,466,331 A | 8/1984 | Matheson |
| 4,536,893 A | 8/1985 | Parravicini |
| 4,567,900 A | 2/1986 | Moore |
| 4,598,039 A | 7/1986 | Fischer et al. |
| 4,630,597 A | 12/1986 | Kantrowitz et al. |
| 4,637,377 A | 1/1987 | Loop |
| 4,690,134 A | 9/1987 | Snyders |
| 4,790,850 A | 12/1988 | Dunn et al. |
| 4,821,723 A | 4/1989 | Baker, Jr. et al. |
| 4,827,932 A | 5/1989 | Ideker et al. |
| 4,834,707 A | 5/1989 | Evans |
| 4,840,626 A | 6/1989 | Linsky et al. |
| 4,878,890 A | 11/1989 | Bilweis |
| 4,932,972 A | 6/1990 | Dunn et al. |
| 4,936,857 A | 6/1990 | Kulik |
| 4,957,477 A | 9/1990 | Lundback |
| 4,973,300 A | 11/1990 | Wright |
| 4,976,730 A | 12/1990 | Kwan-Gett |
| 4,984,584 A | 1/1991 | Hansen et al. |
| 4,995,857 A | 2/1991 | Arnold |
| 5,042,463 A | 8/1991 | Lekholm |
| 5,057,117 A | 10/1991 | Atweh |
| 5,074,129 A | 12/1991 | Matthew |
| 5,087,243 A | 2/1992 | Avitall |
| 5,131,905 A | 7/1992 | Grooters |
| 5,150,706 A | 9/1992 | Cox et al. |
| 5,186,711 A | 2/1993 | Epstein |
| 5,188,813 A | 2/1993 | Fairey et al. |
| 5,192,314 A | 3/1993 | Daskalakis |
| 5,207,725 A | 5/1993 | Pinkerton |
| 5,224,363 A | 7/1993 | Sutton |
| 5,256,132 A | 10/1993 | Snyders |
| 5,279,539 A | 1/1994 | Bohan et al. |
| 5,290,217 A | 3/1994 | Campos |
| 5,336,253 A | 8/1994 | Gordon et al. |
| 5,339,657 A | 8/1994 | McMurray |
| 5,341,815 A | 8/1994 | Cofone et al. |
| 5,356,432 A | 10/1994 | Rutkow et al. |
| 5,366,460 A | 11/1994 | Eberbach |
| 5,383,840 A | 1/1995 | Heilman et al. |
| 5,385,156 A | 1/1995 | Oliva |
| 5,405,360 A | 4/1995 | Tovey |
| 5,409,703 A | 4/1995 | McAnalley et al. |
| 5,429,584 A | 7/1995 | Chiu |
| 5,507,779 A | 4/1996 | Altman |
| 5,524,633 A | 6/1996 | Heaven et al. |
| 5,533,958 A | 7/1996 | Wilk |
| 5,558,617 A | 9/1996 | Heilman et al. |
| 5,593,441 A | 1/1997 | Lichtenstein et al. |
| 5,603,337 A | 2/1997 | Jarvik |
| 5,611,515 A | 3/1997 | Benderev et al. |
| 5,647,380 A | 7/1997 | Campbell et al. |
| 5,695,525 A | 12/1997 | Mulhauser et al. |
| 5,702,343 A | 12/1997 | Alferness |
| 5,713,954 A | 2/1998 | Rosenberg et al. |
| 5,735,290 A | 4/1998 | Sterman et al. |
| 5,766,216 A | 6/1998 | Gangal et al. |
| 5,782,746 A | 7/1998 | Wright |
| D399,000 S | 9/1998 | Rothman et al. |
| 5,800,334 A | 9/1998 | Wilk |
| 5,800,528 A | 9/1998 | Lederman et al. |
| 5,839,842 A | 11/1998 | Wanat et al. |
| 5,848,962 A | 12/1998 | Feindt |
| 5,853,422 A | 12/1998 | Huebsch et al. |
| 5,928,250 A | 7/1999 | Koike et al. |
| 5,931,810 A | 8/1999 | Grabek |
| 5,961,440 A | 10/1999 | Schweich, Jr. et al. |
| 5,972,013 A | 10/1999 | Schmidt |
| 5,976,551 A | 11/1999 | Mottez et al. |
| 5,990,378 A | 11/1999 | Ellis |
| 6,042,536 A | 3/2000 | Tihon et al. |
| 6,045,497 A | 4/2000 | Schweich, Jr. et al. |
| 6,050,936 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,085,754 A | 7/2000 | Alferness et al. |
| 6,089,051 A | 7/2000 | Gorywoda et al. |
| 6,095,968 A | 8/2000 | Snyders |
| 6,123,662 A | 9/2000 | Alferness |
| 6,126,590 A | 10/2000 | Alferness |
| 6,155,968 A | 12/2000 | Wilk |
| 6,155,972 A | 12/2000 | Nauertz et al. |
| 6,162,168 A | 12/2000 | Schweich, Jr. et al. |
| 6,165,119 A | 12/2000 | Schweich, Jr. et al. |
| 6,165,120 A | 12/2000 | Schweich, Jr. et al. |
| 6,165,121 A | 12/2000 | Alferness |
| 6,165,122 A | 12/2000 | Alferness |
| 6,169,922 B1 | 1/2001 | Alferness et al. |
| 6,174,279 B1 | 1/2001 | Girard |
| 6,179,791 B1 | 1/2001 | Krueger |
| 6,183,411 B1 | 2/2001 | Mortier et al. |
| 6,190,408 B1 | 2/2001 | Melvin |
| 6,193,646 B1 | 2/2001 | Kulisz et al. |
| 6,193,648 B1 | 2/2001 | Krueger |
| 6,205,747 B1 | 3/2001 | Paniagua Olaechea |
| 6,206,004 B1 | 3/2001 | Schmidt et al. |
| 6,206,820 B1 | 3/2001 | Kazi |
| 6,221,103 B1 | 4/2001 | Melvin |
| 6,224,540 B1 | 5/2001 | Lederman et al. |
| 6,230,714 B1 | 5/2001 | Alferness et al. |
| 6,241,654 B1 | 6/2001 | Alferness |
| 6,260,552 B1 | 7/2001 | Mortier et al. |
| 6,261,222 B1 | 7/2001 | Schweich, Jr. et al. |
| 6,264,602 B1 | 7/2001 | Mortier et al. |
| 6,293,906 B1 | 9/2001 | Vanden Hoek et al. |
| 6,332,863 B1 | 12/2001 | Schweich, Jr. et al. |
| 6,332,864 B1 | 12/2001 | Schweich, Jr. et al. |
| 6,332,893 B1 | 12/2001 | Mortier et al. |

(56) References Cited

U.S. PATENT DOCUMENTS

| | | |
|---|---|---|
| 6,360,749 B1 | 3/2002 | Jayaraman |
| 6,370,429 B1 | 4/2002 | Alferness et al. |
| 6,375,608 B1 | 4/2002 | Alferness |
| 6,402,679 B1 | 6/2002 | Mortier |
| 6,402,680 B2 | 6/2002 | Mortier |
| 6,406,420 B1 | 6/2002 | McCarthy et al. |
| 6,409,760 B1 | 6/2002 | Melvin |
| 6,416,459 B1 | 7/2002 | Haindl |
| 6,425,856 B1 | 7/2002 | Shapland et al. |
| 6,432,039 B1 | 8/2002 | Wardle |
| 6,482,146 B1 | 11/2002 | Alferness et al. |
| 6,488,618 B1 | 12/2002 | Paolitto et al. |
| 6,494,825 B1 | 12/2002 | Talpade |
| 6,508,756 B1 | 1/2003 | Kung et al. |
| 6,514,194 B2 | 2/2003 | Schweich, Jr. et al. |
| 6,517,570 B1 | 2/2003 | Lau et al. |
| 6,520,904 B1 | 2/2003 | Melvin |
| 6,537,198 B1 | 3/2003 | Vidlund et al. |
| 6,537,203 B1 | 3/2003 | Alferness et al. |
| 6,541,678 B2 | 4/2003 | Klein |
| 6,544,168 B2 | 4/2003 | Alferness |
| 6,547,716 B1 | 4/2003 | Milbocker |
| 6,558,319 B1 | 5/2003 | Aboul-Hosn et al. |
| 6,564,094 B2 | 5/2003 | Alferness et al. |
| 6,567,699 B2 | 5/2003 | Alferness et al. |
| 6,569,082 B1 | 5/2003 | Chin |
| 6,572,533 B1 | 6/2003 | Shapland et al. |
| 6,575,921 B2 | 6/2003 | Vanden Hoek et al. |
| 6,579,226 B2 | 6/2003 | Vanden Hoek et al. |
| 6,582,355 B2 | 6/2003 | Alferness et al. |
| 6,587,734 B2 | 7/2003 | Okuzumi et al. |
| 6,589,160 B2 | 7/2003 | Schweich, Jr. et al. |
| 6,592,514 B2 | 7/2003 | Kolata et al. |
| 6,595,912 B2 | 7/2003 | Lau et al. |
| 6,602,184 B2 | 8/2003 | Lau et al. |
| 6,612,978 B2 | 9/2003 | Lau et al. |
| 6,612,979 B2 | 9/2003 | Lau et al. |
| 6,616,596 B1 | 9/2003 | Milbocker |
| 6,616,684 B1 | 9/2003 | Vidlund et al. |
| 6,620,095 B2 | 9/2003 | Taheri |
| 6,622,730 B2 | 9/2003 | Ekvall et al. |
| 6,629,921 B1 | 10/2003 | Schweich, Jr. et al. |
| 6,645,139 B2 | 11/2003 | Haindl |
| 6,663,558 B2 | 12/2003 | Lau et al. |
| 6,673,009 B1 | 1/2004 | Vanden Hoek et al. |
| 6,682,474 B2 | 1/2004 | Lau et al. |
| 6,682,475 B2 | 1/2004 | Cox et al. |
| 6,682,476 B2 | 1/2004 | Alferness et al. |
| 6,685,627 B2 | 2/2004 | Jayaraman |
| 6,689,048 B2 | 2/2004 | Vanden Hoek et al. |
| 6,695,768 B1 | 2/2004 | Levine et al. |
| 6,695,769 B2 | 2/2004 | French et al. |
| 6,701,929 B2 | 2/2004 | Hussein |
| 6,702,732 B1 | 3/2004 | Lau et al. |
| 6,709,382 B1 | 3/2004 | Horner |
| 6,716,158 B2 | 4/2004 | Raman et al. |
| 6,723,038 B1 | 4/2004 | Schroeder et al. |
| 6,723,041 B2 | 4/2004 | Lau et al. |
| 6,726,696 B1 | 4/2004 | Houser et al. |
| 6,726,920 B1 | 4/2004 | Theeuwes et al. |
| 6,727,316 B1 | 4/2004 | Bremser |
| 6,730,016 B1 | 5/2004 | Cox et al. |
| 6,746,471 B2 | 6/2004 | Mortier et al. |
| 6,755,777 B2 | 6/2004 | Schweich, Jr. et al. |
| 6,755,779 B2 | 6/2004 | Vanden Hoek et al. |
| 6,755,861 B2 | 6/2004 | Nakao |
| 6,764,510 B2 | 7/2004 | Vidlund et al. |
| 6,776,754 B1 | 8/2004 | Wilk |
| 6,793,618 B2 | 9/2004 | Schweich, Jr. et al. |
| 6,808,488 B2 | 10/2004 | Mortier et al. |
| 6,852,075 B1 | 2/2005 | Taylor |
| 6,852,076 B2 | 2/2005 | Nikolic et al. |
| 6,858,001 B1 | 2/2005 | Aboul-Hosn |
| 6,876,887 B2 | 4/2005 | Okuzumi et al. |
| 6,881,185 B2 | 4/2005 | Vanden Hoek et al. |
| 6,893,392 B2 | 5/2005 | Alferness |
| 6,896,652 B2 | 5/2005 | Alferness et al. |
| 6,902,522 B1 | 6/2005 | Walsh et al. |
| 6,902,524 B2 | 6/2005 | Alferness et al. |
| 6,908,426 B2 | 6/2005 | Shapland et al. |
| 6,951,534 B2 | 10/2005 | Girard et al. |
| 6,997,865 B2 | 2/2006 | Alferness et al. |
| 7,022,063 B2 | 4/2006 | Lau et al. |
| 7,022,064 B2 | 4/2006 | Alferness et al. |
| 7,025,719 B2 | 4/2006 | Alferness et al. |
| 7,060,023 B2 | 6/2006 | French et al. |
| 7,077,862 B2 | 7/2006 | Vidlund et al. |
| 7,081,086 B2 | 7/2006 | Lau et al. |
| 7,112,219 B2 | 9/2006 | Vidlund |
| 7,155,295 B2 | 12/2006 | Lau et al. |
| 7,163,507 B2 | 1/2007 | Alferness et al. |
| 7,181,272 B2 | 2/2007 | Struble et al. |
| 7,189,203 B2 | 3/2007 | Lau et al. |
| 7,235,042 B2 | 6/2007 | Vanden Hoek et al. |
| 7,252,632 B2 | 8/2007 | Shapland et al. |
| 7,276,022 B2 | 10/2007 | Lau et al. |
| 7,351,200 B2 | 4/2008 | Alferness |
| 7,398,781 B1 | 7/2008 | Chin |
| 7,404,793 B2 | 7/2008 | Lau |
| 7,410,461 B2 | 8/2008 | Lau et al. |
| 7,468,029 B1 | 12/2008 | Robertson |
| 7,651,462 B2 | 1/2010 | Hjelle et al. |
| 7,955,247 B2 | 6/2011 | Levine et al. |
| 8,092,363 B2 | 1/2012 | Leinsing et al. |
| 8,100,821 B2 | 1/2012 | Hjelle et al. |
| 8,109,868 B2 | 2/2012 | Girard et al. |
| 8,202,212 B2 | 6/2012 | Hjelle et al. |
| 8,277,372 B2 | 10/2012 | Alferness et al. |
| 8,617,051 B2 | 12/2013 | Hjelle et al. |
| 2001/0016675 A1 | 8/2001 | Mortier et al. |
| 2001/0025171 A1 | 9/2001 | Mortier et al. |
| 2002/0019580 A1 | 2/2002 | Lau et al. |
| 2002/0029080 A1 | 3/2002 | Mortier et al. |
| 2002/0045798 A1 | 4/2002 | Lau et al. |
| 2002/0058855 A1 | 5/2002 | Schweich, Jr. et al. |
| 2002/0068849 A1 | 6/2002 | Schweich, Jr. et al. |
| 2002/0068850 A1 | 6/2002 | Vanden Hoek et al. |
| 2002/0077524 A1 | 6/2002 | Schweich, Jr. et al. |
| 2002/0133055 A1 | 9/2002 | Handl |
| 2002/0147406 A1 | 10/2002 | Von Segesser |
| 2002/0151766 A1 | 10/2002 | Shapland |
| 2002/0169358 A1 | 11/2002 | Mortier et al. |
| 2002/0169359 A1 | 11/2002 | McCarthy et al. |
| 2002/0169360 A1 | 11/2002 | Taylor et al. |
| 2002/0173694 A1 | 11/2002 | Mortier et al. |
| 2003/0032979 A1 | 2/2003 | Mortier et al. |
| 2003/0050529 A1 | 3/2003 | Vidlund et al. |
| 2003/0060895 A1 | 3/2003 | French et al. |
| 2003/0065248 A1 | 4/2003 | Lau et al. |
| 2003/0088149 A1 | 5/2003 | Raman et al. |
| 2003/0130731 A1 | 7/2003 | Vidlund et al. |
| 2003/0166992 A1 | 9/2003 | Schweich, Jr. et al. |
| 2003/0171641 A1 | 9/2003 | Schweich, Jr. et al. |
| 2003/0181928 A1 | 9/2003 | Vidlund et al. |
| 2003/0229260 A1 | 12/2003 | Girard et al. |
| 2003/0229265 A1 | 12/2003 | Girard et al. |
| 2003/0233023 A1 | 12/2003 | Khaghani et al. |
| 2004/0002626 A1 | 1/2004 | Feld et al. |
| 2004/0010180 A1 | 1/2004 | Scorvo |
| 2004/0034272 A1 | 2/2004 | Diaz et al. |
| 2004/0059181 A1 | 3/2004 | Alferness |
| 2004/0127983 A1 | 7/2004 | Mortier et al. |
| 2004/0133062 A1 | 7/2004 | Pai et al. |
| 2004/0133063 A1 | 7/2004 | McCarthy et al. |
| 2004/0147805 A1 | 7/2004 | Lau et al. |
| 2004/0147965 A1 | 7/2004 | Berger |
| 2004/0167374 A1 | 8/2004 | Schweich et al. |
| 2004/0181118 A1 | 9/2004 | Kochamba |
| 2004/0181120 A1 | 9/2004 | Kochamba |
| 2004/0181124 A1 | 9/2004 | Alferness |
| 2004/0186342 A1 | 9/2004 | Vanden Hock et al. |
| 2004/0210104 A1 | 10/2004 | Lau et al. |
| 2004/0215308 A1 | 10/2004 | Bardy et al. |
| 2004/0225304 A1 | 11/2004 | Vidlund et al. |

(56) References Cited

U.S. PATENT DOCUMENTS

| | | |
|---|---|---|
| 2004/0243229 A1 | 12/2004 | Vidlund et al. |
| 2004/0249242 A1 | 12/2004 | Lau et al. |
| 2004/0267083 A1 | 12/2004 | McCarthy et al. |
| 2004/0267329 A1 | 12/2004 | Raman et al. |
| 2005/0004428 A1 | 1/2005 | Cox et al. |
| 2005/0010079 A1 | 1/2005 | Bertolero et al. |
| 2005/0014992 A1 | 1/2005 | Lilip et al. |
| 2005/0020874 A1 | 1/2005 | Lau et al. |
| 2005/0033109 A1 | 2/2005 | Lau et al. |
| 2005/0038316 A1 | 2/2005 | Taylor |
| 2005/0054892 A1 | 3/2005 | Lau et al. |
| 2005/0058853 A1 | 3/2005 | Kochambe |
| 2005/0059854 A1 | 3/2005 | Hoek et al. |
| 2005/0059855 A1 | 3/2005 | Lau et al. |
| 2005/0065396 A1 | 3/2005 | Mortier et al. |
| 2005/0075723 A1 | 4/2005 | Schroeder et al. |
| 2005/0085688 A1 | 4/2005 | Girard et al. |
| 2005/0090707 A1 | 4/2005 | Lau et al. |
| 2005/0133941 A1 | 6/2005 | Schuhmacher |
| 2005/0171589 A1 | 8/2005 | Lau et al. |
| 2005/0192474 A1 | 9/2005 | Vanden Hoek et al. |
| 2005/0228217 A1 | 10/2005 | Alferness et al. |
| 2005/0256368 A1 | 11/2005 | Klenk et al. |
| 2005/0283042 A1 | 12/2005 | Meyer et al. |
| 2005/0288715 A1 | 12/2005 | Lau et al. |
| 2006/0009831 A1 | 1/2006 | Lau et al. |
| 2006/0052660 A1 | 3/2006 | Chin |
| 2006/0063970 A1 | 3/2006 | Raman et al. |
| 2006/0155165 A1 | 7/2006 | Vanden Hoek et al. |
| 2006/0229490 A1 | 10/2006 | Chin |
| 2006/0270896 A1 | 11/2006 | Dietz et al. |
| 2007/0032696 A1 | 2/2007 | Duong |
| 2007/0043416 A1 | 2/2007 | Callas et al. |
| 2007/0208211 A1 | 9/2007 | Alferness et al. |
| 2007/0208215 A1 | 9/2007 | Hjelle |
| 2007/0219407 A1 | 9/2007 | Vanden Hoek et al. |
| 2007/0225547 A1 | 9/2007 | Alferness et al. |
| 2008/0033234 A1 | 2/2008 | Hjelle et al. |
| 2008/0064917 A1 | 3/2008 | Bar et al. |
| 2009/0062596 A1 | 3/2009 | Leinsing et al. |
| 2009/0131743 A1 | 5/2009 | Hjelle et al. |
| 2010/0004504 A1 | 1/2010 | Callas |
| 2010/0094080 A1 | 5/2010 | Hjelle et al. |
| 2010/0160721 A1 | 6/2010 | Alferness et al. |
| 2010/0185050 A1 | 7/2010 | Alferness et al. |
| 2010/0268019 A1 | 10/2010 | Hjelle et al. |
| 2012/0253112 A1 | 10/2012 | Hjelle et al. |
| 2014/0181124 A1 | 9/2014 | Hofmeier et al. |

FOREIGN PATENT DOCUMENTS

| | | |
|---|---|---|
| EP | 0280564 | 8/1988 |
| EP | 0303719 | 2/1989 |
| EP | 0557964 | 9/1993 |
| GB | 2209678 | 5/1989 |
| JP | 01-145066 | 6/1989 |
| JP | 02-271829 | 11/1990 |
| JP | 2002-532189 | 10/2002 |
| SU | 1009457 | 4/1983 |
| WO | WO 1993/03685 | 3/1993 |
| WO | WO 1996/16601 | 6/1996 |
| WO | WO 1996/31175 | 10/1996 |
| WO | WO 1998/14136 | 4/1998 |
| WO | WO 1998/29041 | 7/1998 |
| WO | WO 1998/35632 | 8/1998 |
| WO | WO 1998/58598 | 12/1998 |
| WO | WO 1999/44534 | 9/1999 |
| WO | WO 1999/52470 | 10/1999 |
| WO | WO 1999/52471 | 10/1999 |
| WO | WO 2000/02500 | 1/2000 |
| WO | WO 2000/06026 | 2/2000 |
| WO | WO 2000/06027 | 2/2000 |
| WO | WO 2000/06028 | 2/2000 |
| WO | WO 2000/16700 | 3/2000 |
| WO | WO 2000/28912 | 5/2000 |
| WO | WO 2000/28918 | 5/2000 |
| WO | WO 00/36995 | 6/2000 |
| WO | WO 2001/002500 | 1/2001 |
| WO | WO 2001/003608 | 1/2001 |
| WO | WO 2001/010421 | 2/2001 |
| WO | WO 2001/067985 | 9/2001 |
| WO | WO 2001/091667 | 12/2001 |
| WO | WO 2001/095830 | 12/2001 |
| WO | WO 2002/013726 | 2/2002 |
| WO | WO 2002/000099 | 9/2002 |
| WO | WO 2003/022131 | 3/2003 |
| WO | WO 2006/023580 | 3/2006 |
| WO | WO 2008/011411 | 1/2008 |
| WO | WO 2010/111592 | 9/2010 |

OTHER PUBLICATIONS

U.S. Appl. No. 14/053,261, filed Oct. 16, 2013, Hjelle et al.
U.S. Appl. No. 14/053,587, filed Oct. 14, 2013, Hjelle et al.
U.S. Appl. No. 14/053,590, filed Oct. 14, 2013, Hjelle et al.
U.S. Appl. No. 29/469,753, filed Oct. 14, 2013, Hjelle et al.
U.S. Appl. No. 60/148,130, filed Aug. 10, 1999, Chin.
U.S. Appl. No. 60/150,737, filed Aug. 25, 1999, Chin.
Bolling, et al., "Intermediate-Term Outcome of Mitral Reconstruction in Cardiomyopathy", *J Thorac. Cardiovasc. Surg.*, Feb. 1998, 115(2):381-388.
Bourge, "Clinical Trial Begins for Innovative Device-Altering Left Ventricular Shape in Heart Failure", UAB Insight, posted Aug. 8, 2012, retrieved Jun. 17, 2004, http://www.health.uab.edu/show, 2 pages.
Capomolla et al., "Dobutamine and nitroprusside infusion in patients with severe congestive heart failure: Hemodynamic improvement by discordant effects on mitral regurgitation, left atrial function, and ventricular function", *American Heart Journal*, Dec. 1997, 1089-1098.
Capouya et al., "Girdling Effect of Nonstimulated Cardiomyoplasty on Left Ventricular Function", *Ann Thorac. Surg.*, 1993, 56:867-871.
Cohn, "The Management of Chronic Heart Failure", *The New England Journal of Medicine*, Aug. 15, 1996, 335(7): 490-498.
Coletta et al., "Prognostic value of left ventricular volume response during dobutamine stress echocardiography," *European Heart Journal*, Oct. 1997, 18: 1599-1605.
Daubeney et al., "Pulmonary Atresia/Intact Ventricular Septum: Early Outcome After Right Ventricular Outflow Reconstruction by Surgery or Catheter Intervention," Supplement to Circulation, Oct. 15, 1995, 92(8), Abstract 1812.
DeVries et al., "A Novel Technique for Measurement of Pericardial Balloon," *Am. J Physiol Heart Circ Physiol*, Jan. 2001, 280(6):H2815-H2822.
Ghanta, et al., "Cardiovascular Surgery: Adjustable, Physiological Ventricular Restraint Improves Left Ventricular Mechanics and Reduces Dilation in an Ovine Model of Chronic Heart Failure," *Circulation, JAHA*, 2007, 115:1201-10.
Guasp., "Una protesis contentiva para el tratamiento de la miocardiopatia dilatada," *Revista Espanola de Cardiologia*, Jul. 1998, 51(7): 521-528.
Hamilton et al., "Static and Dynamic Operating Characteristics of a Pericardial Balloon," *J Appl. Physiol*, Apr. 2001, 90(4):1481-1488.
Hung, et al., "Persistent Reduction of Ischemic Mitral Regurgitation by Papillary Muscle Repositioning: Structural Stabilization of the Pipillary Muscle Ventricular Wall Complex," *Circulation, JAHA*, 2007, 116:1-259 1-263.
Justo et al., "Outcomes of Transcatheter Perforation of the Right Ventricular Outflow Tract as Primary Management for Pulmonary Valve Atresia in the Newborn," Supplement to Circulation, Oct. 15, 1995, 92(8), Abstract 1813.
Kass et al., "Reverse Remodeling From Cardiomyoplasty in Human Heart Failure External Constraint Versus Active Assist," *Circulation*, May 1, 1995, 91(9):2314-2318, retrieved Jan. 16, 2014, http://circ.ahajournals.org/content/91/9/2314.full.

(56) References Cited

OTHER PUBLICATIONS

Labrousse, Louis et al., "Implantation of a Cardiac Support Device by the 'Parachute-Like' Technique Through Sternal and Trans-Abdominal Approach," Abstract, *94 Programme of the 4th EACTSIESTS Joint Meeting*, Sep. 28, 2005, Barcelona, Spain.

Lamas, et al., "Clinical Significance of Mitral Regurgitation After Acute Myocardial Infarction," *Circulation-JAHA*, Aug. 5, 1997, 96(3):827-833, retrieved Jan. 16, 2014, http://circ.ahajournals.org/content/96/3/827.long.

Lei-Cohen, et al., "Design of a New Surgical Approach for Ventricular Remodeling to Relieve Ischemic Mitral Regurgitation," *Circulation*, Jun. 13, 2000, 101:2756-2763.

Levin et al., "Reversal of Chronic Ventricular Dilation in Patients with End-Stage Cardiomyopathy by Prolonged Mechanical Unloading," *Circulation*, Jun. 1, 1995, 91(11): 2717-2720, retrieved Jan. 16, 2014, http://circ.ahajournals.org/content/91/11/2717.long.

Lloyd et al.. "The PDA Coil Registry: Report of the First 535 Procedures," Supplement to Circulation, Oct. 15, 1995, 92(8), Abstract 1811.

Oh et al., "The Effects of Prosthetic Cardiac Binding and Adynamic Cardiomyoplasty in a Model of Dilated Cardiomyopathy," *The Journal of Thoracic and Cardiovascular Surgery*, Jul. 1998, 116(1):148-153.

Pai, et al., "Valvular Egurgitation," *Clinical Science Abstracts*, 2000, 1800-1804.

Paling, "Two-Bar Fabrics (Part-Set Threading)", *Warp Knitting Technology*, Columbine Press (Publishers) Ltd., Buxton, Great Britain, p. III (1970).

Timek, et al., "Pathogenesis of Mitral Regurgitation in Tachycardia Induced Cardiomyopathy," Circulation-JAHA, 2001, 104:1-47-1-53.

Vaynblat et al., "Cardiac Binding in Experimental Heart Failure," *Ann. Thorac. Surg.*, 1994, vol. 64, 11 pages.

Vinereanu, et al., "'Pure' diastolic dysfunction is associated with long-axis systolic dysfunction. Implications for the diagnosis and classification of hear failure," *European Journal of Heart Failure*, Aug. 2005, 7(5): 820-828 (Abstract Only).

International Search Report and Written Opinion in International Application No. PCT/US2013/064894, dated Apr. 3, 2014, 27 pages.

International Search Report and Written Opinion in International Application No. PCT/US2013/064895, dated Apr. 21, 2014, 14 pages.

CARDIAC TREATMENT SYSTEM

CROSS-REFERENCE TO RELATED APPLICATION(S)

This application is a continuation of U.S. application Ser. No. 14/053,261 filed on Oct. 14, 2013, which claims priority to U.S. Provisional Application Ser. No. 61/713,351 filed on Oct. 12, 2012, the contents of this aforementioned application being fully incorporated herein by reference.

TECHNICAL FIELD

The present disclosure relates to medical devices for treating heart diseases and valvular dysfunction, including valvular regurgitation.

BACKGROUND OF THE INVENTION

Various compression-style systems currently exist for treating heart diseases and conditions such as congestive heart disease and valvular dysfunction. These systems typically involve either: (a) jackets that are placed around the heart to limit heart expansion to treat congestive heart disease, or (b) bands that are placed around the heart with fillable chambers to exert localized pressure to re-form the shape of heart valves, for example to minimize valve leakage.

An example of the former is found in the Acorn Cardiovascular Inc. system set forth in U.S. Published Patent Application 2010/0160721 entitled "Cardiac Support Device With Differential Compliance." This device is used to treat congestive heart disease. Congestive heart disease is the progressive enlargement of the heart. This enlargement requires the heart to perform an increasing amount of work. In time, the heart cannot supply an adequate amount of blood, resulting in a patient that is fatigued and in discomfort. The Acorn Cardiovascular Inc. system is a cardiac support device that limits heart expansion using a flexible jacket positioned around the heart. In operation, the jacket surrounds the myocardium and provides reduced expansion of the heart during diastole. The jacket has upper and lower ends. The upper end is open. The lower end may be open or closed. The jacket is sized for the particular heart to be contained within its volume. When placed on the heart, the upper end of the jacket extends up to the valvular annulus and terminates along the AV groove. The jacket itself further extends down to constrain the lower ventricular extremities. In this position, the jacket provides sufficient constraint at the valvular annulus. Alternatively, the jacket may not cover the apex of the heart (but it will cover its left and right ventricles). This placement is desirable as it presents a constraint against enlargement of the ventricular walls of the heart. After the jacket is positioned on the heart, it can then be secured to the heart, for example, by suturing at various locations around its circumference. However, it is preferred to avoid excessive suturing locations as this would restrict contraction of the heart during systole. Once placed, the jacket's volume and shape can be adjusted by gathering together and suturing excess material. Specifically, the jacket is adjusted to be snug during diastole (without being too tight such that left ventricular pressure will rise). The jacket then constrains enlargement of the heart beyond this volume.

An example of the second type of system is found in Mardil, Inc.'s U.S. Pat. No. 8,092,363 entitled "Heart Band With Fillable Chambers To Modify Heart Valve Function." This device has a plurality of fillable chambers that exert inward radial forces on heart valves. These fillable chambers are disposed within the inner and outer layers of a silicone rubber band. In operation, this device is used to treat dilation of heart valves by applying localized pressure to the surface of the heart. For example, a pair of these fillable chambers positioned on either side of the mitral valve can be used to re-shape the mitral valve such that mitral valve leakage is minimized or stopped.

As can be seen, these two above systems operate quite differently on the patient's heart. The first (i.e.: Acorn) system stabilizes the base of the heart, but does not provide localized therapeutic pressure on the heart valves. The second (i.e. Mardil) system provides localized pressure to heart valves through all heart phases; however, it does not stabilize the base of the heart.

It would instead be desirable to provide a system that permits localized pressure on selected regions of the heart (similar to the Mardill '363 device), but avoids its use of a solid silicone rubber band wrapped around the heart that may interfere with contraction and dilation.

It would also be advantageous to provide a system that provides localized pressure on the heart and also offers the advantages of a knit mesh jacket. Advantages of a knit mesh could include the fact that it allows for more freedom in heart contraction and dilation. In addition, a mesh band will advantageously self-attach to the heart by way of fibrotic encapsulation. This would assist in positioning the inflatable bladder(s) at a desired location and preventing unwanted movement of the bladder(s) in the future.

SUMMARY

In preferred aspects, some embodiments described herein provide a mesh structure (which may be polyester) to position a bladder for deformation of the mitral valve or papillary muscle to decrease valvular regurgitation.

Particular embodiments of the present invention provide a system for providing localized pressure on regions of a patient's heart to treat various heart problems. In various applications, it can be used to apply pressure to the mitral valve to reshape the valve and prevent mitral regurgitation, or to the papillary muscle to prevent mitral regurgitation (by relieving tension on the chordae which prohibits proper valve function), or to the tricuspid valve to prevent regurgitation. With regard to the mitral valve, the anatomical target for deformation is the P2 area of the valve. By pressing on this spot, the distance across the valve is artificially reduced, thereby preventing the gap in the valve responsible for the regurgitation.

In preferred embodiments, the system comprises a jacket received around the heart, with one or more inflatable bladders positioned inside this jacket. The bladder(s) are differentially expandable such that they have an inner (heart-facing) surface that is more compliant than their outer (jacket-facing) surface. As a result, when the bladder(s) is inflated, its inner surface expands more than its outer surface (which may not expand at all). As such, the inflated bladder exerts an inward pressure on a localized region of the heart.

In one aspect, some embodiments described herein provide an assembly for providing localized pressure to a region of a patient's heart to improve heart functioning, comprising: (a) a jacket made of a flexible biocompatible material, the jacket having an open top end that is received around the heart and a bottom portion that is received around the apex of the heart; and (b) at least one inflatable bladder disposed on an interior surface of the jacket, the inflatable bladder having an inelastic outer (jacket facing) surface positioned adjacent to the jacket and an elastic inner (heart facing) surface such that inflation of the bladder causes the bladder to deform substantially inwardly to exert localized pressure against a region of the heart.

In another aspect, particular embodiments of the present invention provide a method of providing localized pressure to a region of a patient's heart to improve heart functioning, comprising: (a) positioning an assembly around a patient's heart, wherein the assembly comprises: a jacket and at least one inflatable bladder, wherein the jacket is made of a flexible biocompatible material having an open top end that is received around the heart and a bottom portion that is received around the apex of the heart, and the inflatable bladder is disposed on an interior surface of the jacket, the inflatable bladder having an inelastic outer surface positioned adjacent to the jacket and an elastic inner surface; and (b) inflating the bladder causing the bladder to expand such that the bladder deforms substantially inwardly to exert localized pressure against a region of the heart.

An important advantage of some embodiments of the system described herein not seen in existing systems is that its bladder(s) are differentially expandable, meaning that one side of the bladder expands more than the other when it is inflated. This provides very precisely targeted pressure to specific regions of the heart.

Another advantage of the some embodiments of the system described herein is that it uses a mesh jacket to support and position the inflatable bladder(s). An advantage of using a knit mesh (as opposed to a polymer band) to hold the bladder in position is that the mesh is self-attaching to the heart (i.e.: after fibrotic encapsulation). Moreover, there is an anticipated benefit for many patients as the mesh jacket can itself be used to treat the problem of congestive heart disease concurrently with bladder(s) treating valve leakage problems.

In preferred embodiments, the jacket has an elastic band with radiopaque markers at its open top end. With these features, the jacket can then be easily guided and placed at the heart's A-V groove. This makes it easy to position the inflatable bladder(s) at the desired locations on the patient's heart.

DETAILED DESCRIPTION

Particular embodiments of the present invention provide an assembly for providing localized pressure to a region of a patient's heart. As will be described below, some embodiments described herein provide a jacket with one or more inflatable bladders received therein. Thus, the bladder(s) are positioned between the patient's heart and the jacket when the jacket is slipped over the heart.

Figure 1A:
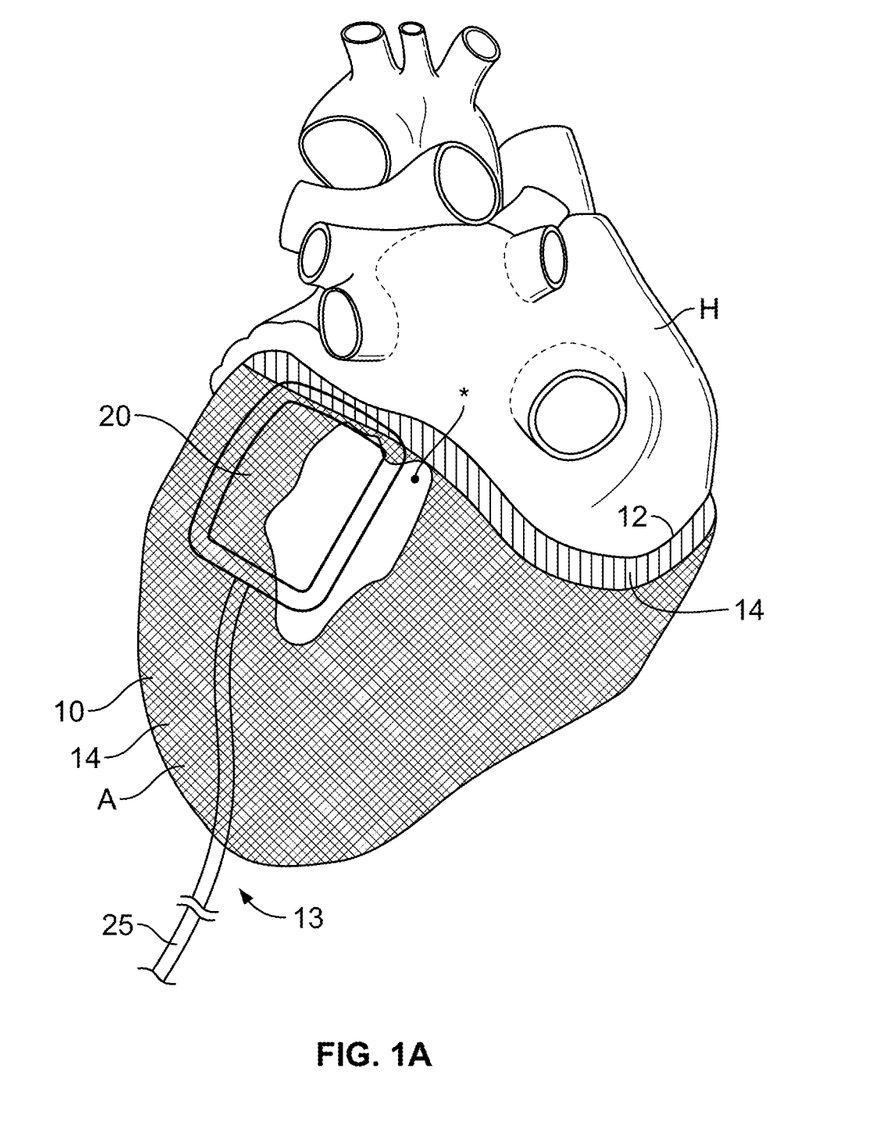
FIG. 1A is a perspective view of the present assembly positioned on a patient's heart, showing an inflatable bladder positioned adjacent to the mitral valve.
Figure 1B:
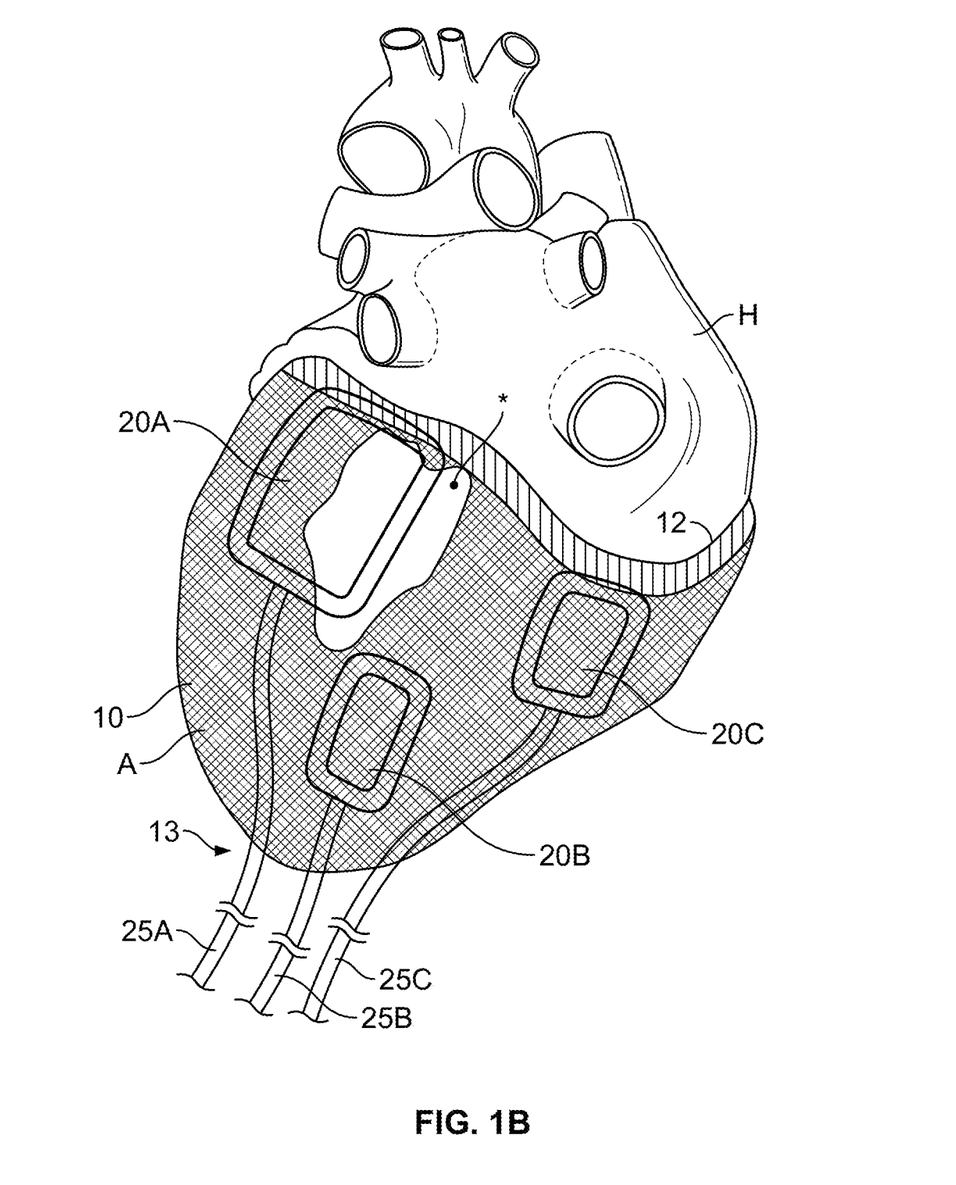
FIG. 1B is a view similar to FIG. 1A, but showing three optional bladder locations at the mitral valve, papillary muscle and tricuspid valve.

FIGS. 1A and 1B show embodiments having one or more inflatable bladders, as follows. In FIG. 1A, the inflatable bladder is positioned adjacent to the patient's mitral valve. FIG. 1B shows additional placement locations of bladders adjacent to the papillary muscle and tricuspid valve. It is to be understood that the description herein encompasses embodiments with only one or with more than one inflatable bladder. Thus, FIGS. 1A and 1B simply show preferred locations for the bladder placement(s).

Figure 2:
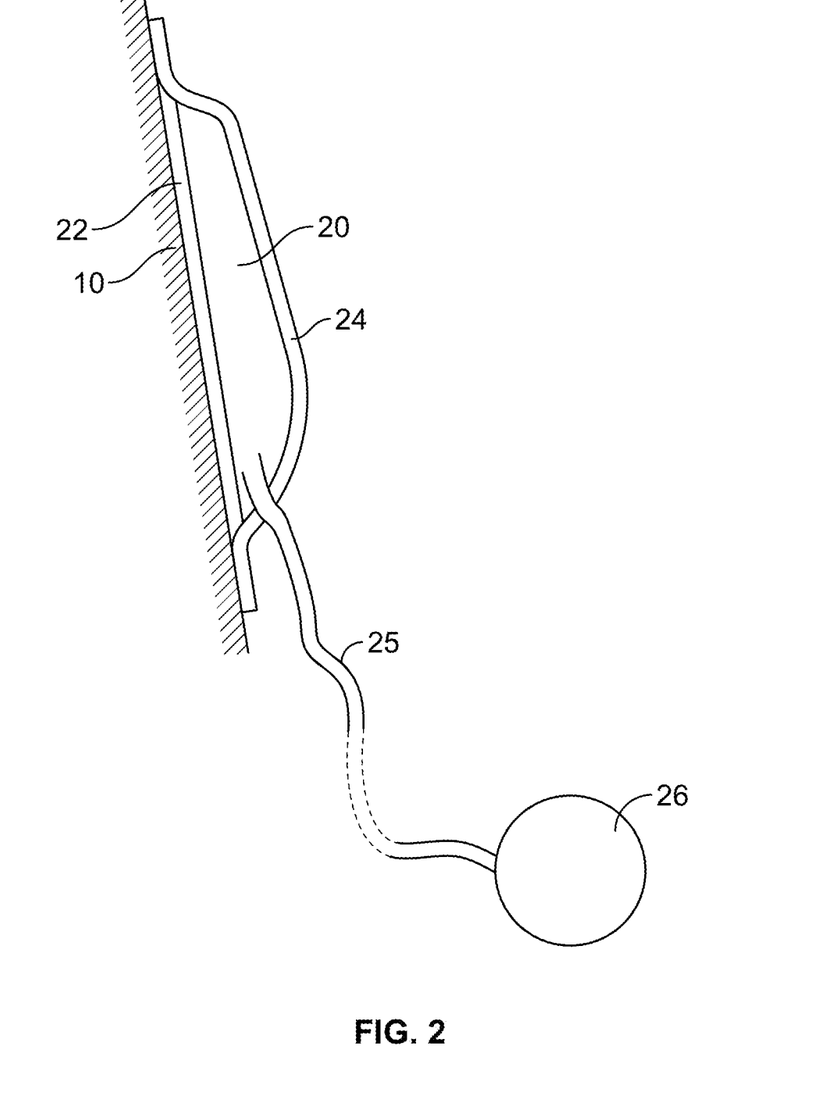
FIG. 2 is a sectional elevation view through one of the inflatable bladders.

As seen in FIGS. 1A-B and 2, the depicted embodiment provides an assembly comprising: a jacket 10 and at least one inflatable bladder 20. Jacket 10 is made of a flexible biocompatible material and has an open top end 12 that is received around the heart H and a bottom portion 14 that is received around the apex A of the heart. In optional aspects, jacket 10 may be made of a knit mesh. This knit mesh may optionally be made of a polymer, including but not limited to high-density polyethylene. Alternatively, jacket 10 may be made of metal.

In one preferred embodiment, jacket 10 is made of a suitable knit material. An example of such a knit material may be the well known "Atlas Knit" material, being a knit structure formed from generally inelastic fibers. In an Atlas Knit, the fibers are interwoven into sets of parallel spaced-apart strands. In response to the low pressures of the heart during diastole, the fibers are generally non-elastic. Alternatively, jacket 10 may be elastic. Optionally, the fibers may be made of Denier polyester. However, other suitable materials, including but not limited to, PTFE, ePTFE, polypropylene and stainless steel may also be used. Advantages of using a knit material include flexibility, fluid permeability and minimizing the amount of heart surface area in direct contact with the jacket (thereby minimizing the potential of scar tissue development).

Inflatable bladder 20 is disposed on an interior surface of jacket 10. Bladder 20 may or may not be attached to jacket 10. FIG. 1B illustrates three separate inflatable bladders 20, being positioned at the mitral valve (bladder 20A), the papillary muscle (bladder 20B) and the tricuspid valve (bladder 20C). When bladder 20 is positioned adjacent to the mitral valve, it is preferably positioned at the P2 area of the valve (in the center of the posterior leaflet) to reduce the distance across the valve, thereby reducing the gap in the valve responsible for the regurgitation. When bladder 20 is positioned adjacent to the tricuspid valve, it performs a similar function, reducing regurgitation through the tricuspid valve. When bladder 20 is positioned adjacent to the papillary muscle, it gently corrects papillary muscle position and relieves tension on the chordae (which otherwise prohibits normal valve functioning).

As seen in FIG. 2, inflatable bladder 20 has an inelastic outer surface 22 positioned adjacent to jacket 10 and an elastic inner surface 24 positioned adjacent to the heart. Bladder 20 may optionally be made of silicon. In preferred aspects, jacket 10 is inelastic, the outer surface 22 of bladder 20 positioned adjacent to the bladder is inelastic and the inner surface 24 of bladder 10 is elastic. As a result, when inflated through fluid supply line 25, inflation of bladder 20 causes the bladder to deform substantially inwardly (i.e.: towards the heart). This then exerts localized pressure against a region of the heart. As can be seen, supply line(s) 25 are preferably positioned inside jacket 10 and extend out of an open bottom end 13 of the jacket adjacent to the apex of the heart. Bottom end 13 may be cinched closed after the jacket 10 has been positioned around the heart.

In preferred aspects, bladder 20 may be is inflated with fluids including air, inert gasses (such as fluorocarbons), silicone gel, saline and contrast agents. Supply lines 25 may optionally be inflated through a blunt needle port, a Luer port fitting, a subcutaneous port 26, etc. Supply lines 25 are made of a suitable bio-compatible material, including but not limited to silicone. The present invention preferably includes mechanisms for inflating and deflating bladders 20 post-implementation. For example, in one approach the device is first received onto the heart. After a period of time (e.g.: 30 days) fibrotic encapsulation of mesh jacket 10 will have occurred. At this time, the bladder(s) 20 can then be inflated (through supply line 25 using a needle to percutaneously access filling reservoir 26. Thus, subcutaneous ports 26 are useful for percutaneous inflation and deflation for therapy optimization or abandonment. Alternatively, the fluid path tube may stay in the intercostal space and be accessed by a small "cut-down" procedure to access the tube.

In optional embodiments, jacket 10 has an elastic band 14 passing around its top end 12. In addition, radiopaque markers 15 can also be provided around top end 12.

The present jacket and bladder system can be placed around the patient's heart in a variety of different approaches. In a preferred method of use, the present system further includes a delivery device for positioning the jacket onto the heart. Exemplary jacket designs and methods of placement are illustrated in US Published Patent Application 2010/0160721, incorporated herein by reference in its entirety. In one preferred aspect of the method, the assembly is implanted into the patient in a left intercostal minithoracotomy using contrast pericardiography and fluoroscopic visualization. After opening the parietal pericardium, the lower portion of the heart is free for applying the jacket over the apex. An example system for positioning the jacket is found in U.S. Pat. No. 5,702,343, incorporated herein by reference.

Particular embodiments described herein also include a preferred method of providing localized pressure to a region of a patient's heart H to improve heart functioning, by: (a) positioning an assembly around a patient's heart, wherein the assembly comprises: a jacket 10 and at least one inflatable bladder 20, wherein jacket 10 is made of a flexible biocompatible material having an open top end 12 that is received around the heart and a bottom portion 14 that is received around the apex of the heart, and the inflatable bladder 20 is disposed on an interior surface of the jacket, and the inflatable bladder 20 has an inelastic outer surface positioned adjacent to the jacket and an elastic inner surface. Next, bladder 20 is inflated causing it to expand such that the bladder deforms substantially inwardly to exert localized pressure against a region of the heart.

In another method of use, Pericardial Edge Management Strips (PEMS) are used. PEMS are sheets having one "peel and stick" side, and may be made of Teflon. These sheets can be used to keep the opening into the pericardium open to facilitate insertion of the device without damage to the pericardium (i.e.: the insertion tool getting hung up on the edges of the opening). In addition, Epicardial Management Strips (EMS) can be used to initially separate the heart from the mesh fabric. After the EMS are pulled out, the jacket fabric can then engage the heart.

An example of a suitable system for measuring the size of the heart is illustrated in International Patent Publication WO 2010/111592, entitled Intra-Operative Heart Size Measuring Tool. This device has a flexible measuring cord with length indicia that is placed around the heart. The distal end of the tool can be inserted through an opening in the patient's chest and pericardium and then positioned at a measurement position at the apex of the patient's heart. Circumference measurements can be made at the A-V groove or at other heart locations, as desired.

What is claimed is:

1. A cardiac implant for implantation around an exterior of a heart, the cardiac implant comprising:
   a mesh jacket configured for implantation circumferentially around ventricles of the heart, the mesh jacket including an open top end configured to be positioned in an atrial-ventricular (A-V) groove of the heart;
   a first inflatable bladder comprising an inner wall and an outer wall, wherein the inner wall itself is more expandable than the outer wall itself such that the first inflatable bladder itself is configured to deform substantially inwardly to exert localized pressure against a region of the heart when the first inflatable bladder is inflated, the first inflatable bladder positioned adjacent to the jacket and located such that, when the top end is in the A-V groove, the first inflatable bladder is positionable adjacent to a mitral valve of the heart; and
   a second inflatable bladder positioned adjacent to the jacket at a location farther away from the top end than the first inflatable bladder, the second inflatable bladder located such that, when the top end is in the A-V groove, the second inflatable bladder is positionable adjacent to a papillary muscle of the heart.

2. The cardiac implant of claim 1, further comprising a third inflatable bladder positioned adjacent to the jacket.

3. The cardiac implant of claim 2, wherein the third inflatable bladder is located such that, when the top end is in the A-V groove, the third inflatable bladder is positionable adjacent to a tricuspid valve of the heart.

4. The cardiac implant of claim 1, further comprising an elastic band around the top end.

5. The cardiac implant of claim 1, further comprising a plurality of radiopaque markers around the top end such that the radiopaque markers demarcate the top end.

6. The cardiac implant of claim 1, wherein the jacket comprises a polyester.

7. A method of providing localized pressure to regions of a heart to improve heart functioning, the method comprising:
   a) positioning an assembly around the heart, wherein the assembly comprises:
      a jacket comprising a flexible biocompatible material having an open top end that is positioned in an atrial-ventricular (A-V) groove of the heart and a bottom portion that is received around the ventricles of the heart;
      a first inflatable bladder comprising an inner wall and an outer wall, wherein the inner wall itself is more expandable than the outer wall itself such that the first inflatable bladder itself is configured to deform substantially inwardly to exert localized pressure against a region of the heart when the first inflatable bladder is inflated, the first inflatable bladder positioned adjacent to the jacket and located such that, when the top end is in the A-V groove, the first inflatable bladder is positioned adjacent to a mitral valve of the heart; and
      a second inflatable bladder positioned adjacent to the jacket at a location father away from the top end than the first inflatable bladder, the second inflatable bladder located such that, when the top end is in the A-V groove, the second inflatable bladder is positioned adjacent to a papillary muscle of the heart;
   b) inflating the first inflatable bladder such that the first inflatable bladder exerts localized pressure to reshape the mitral valve; and (c) inflating the second inflatable bladder such that the second inflatable bladder exerts localized pressure to reposition the papillary muscle to relieve tension on chordae of the mitral valve.

8. The method of claim 7, further comprising inflating a third inflatable bladder of the assembly to exert a localized pressure on the heart.

9. The method of claim 7, wherein said inflating the first inflatable bladder and said inflating the second inflatable bladder occur after fibrotic encapsulation of the jacket on the heart.

* * * * *

UNITED STATES PATENT AND TRADEMARK OFFICE
CERTIFICATE OF CORRECTION

PATENT NO. : 10,405,981 B2  
APPLICATION NO. : 15/218675  
DATED : September 10, 2019  
INVENTOR(S) : Aaron J. Hjelle et al.

Page 1 of 1

It is certified that error appears in the above-identified patent and that said Letters Patent is hereby corrected as shown below:

In the Claims

Column 6, Line 41, in Claim 7 delete "a)" and insert -- (a) --;

Column 6, Line 60, in Claim 7 after location delete "father" and insert -- farther --.

Signed and Sealed this  
Twelfth Day of November, 2019

Andrei Iancu  
*Director of the United States Patent and Trademark Office*